US012636203B2

(12) United States Patent
Kong et al.

(10) Patent No.: US 12,636,203 B2
(45) Date of Patent: May 26, 2026

(54) ABSORBENT ARTICLE

(71) Applicant: Kimberly-Clark Worldwide, Inc., Neenah, WI (US)

(72) Inventors: Danni Kong, Shanghai (CN); Beibei Su, Shanghai (CN)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 334 days.

(21) Appl. No.: 18/547,899

(22) PCT Filed: Apr. 29, 2021

(86) PCT No.: PCT/CN2021/090913
§ 371 (c)(1),
(2) Date: Aug. 25, 2023

(87) PCT Pub. No.: WO2022/226876
PCT Pub. Date: Nov. 3, 2022

(65) Prior Publication Data
US 2024/0293268 A1     Sep. 5, 2024

(51) Int. Cl.
*A61F 13/15* (2006.01)
*A61F 13/511* (2006.01)
*A61F 13/535* (2006.01)
*A61F 13/513* (2006.01)

(52) U.S. Cl.
CPC ........ *A61F 13/5116* (2013.01); *A61F 13/511* (2013.01); *A61F 13/535* (2013.01); *A61F 2013/51361* (2013.01)

(58) Field of Classification Search
CPC .. A61F 13/5116; A61F 13/535; A61F 13/511; A61F 2013/51361

USPC ..................................................... 604/358.28
See application file for complete search history.

(56) References Cited

U.S. PATENT DOCUMENTS

| | | | |
|---|---|---|---|
| 5,342,342 A | 8/1994 | Kitaoka | |
| 5,447,507 A | 9/1995 | Yamamoto | |
| 5,489,282 A * | 2/1996 | Zehner | C09B 29/0037 |
| | | | 604/385.26 |
| 5,492,751 A * | 2/1996 | Butt, Sr. | D04H 1/559 |
| | | | 604/378 |
| 5,746,732 A * | 5/1998 | Olsson | A61F 13/4752 |
| | | | 604/385.28 |

(Continued)

FOREIGN PATENT DOCUMENTS

| | | |
|---|---|---|
| CN | 1846657 B | 5/2011 |
| CN | 101151009 B | 6/2012 |

(Continued)

*Primary Examiner* — Jacqueline F Stephens
(74) *Attorney, Agent, or Firm* — KIMBERLY-CLARK WORLDWIDE, INC.

(57) ABSTRACT

An absorbent article (10) can have an improved feeling of comfort next to the skin of the wearer. The absorbent article (10) can have a longitudinal direction (X), a transverse direction (Y), and a depth direction (Z). The absorbent article (10) can have a topsheet layer (30), a backsheet layer (40), and an absorbent core (50) positioned between the topsheet layer (30) and the backsheet layer (40). The topsheet layer (30) can have a central layer (32) and a pair of side layers (34, 36). Each of the side layers (34, 36) has a folded portion (90, 124) capable of providing an improved feeling of comfort next to the skin of the wearer.

12 Claims, 8 Drawing Sheets

(56) References Cited

U.S. PATENT DOCUMENTS

| | | | |
|---|---|---|---|
| 5,752,947 A | 5/1998 | Awolin | |
| 6,673,985 B2 | 1/2004 | Mizutani et al. | |
| 7,067,711 B2 | 6/2006 | Kuroda et al. | |
| 7,122,713 B2 | 10/2006 | Komatsu et al. | |
| 7,438,708 B2 | 10/2008 | Kashiwagi et al. | |
| 7,462,174 B2 | 12/2008 | Nishitani et al. | |
| 7,708,725 B2 | 5/2010 | Tamagawa et al. | |
| 7,744,578 B2 | 6/2010 | Tanio et al. | |
| 7,763,001 B2 | 7/2010 | Kawamura | |
| 7,922,706 B2 | 4/2011 | Konawa | |
| 8,251,966 B2 | 8/2012 | Kudo et al. | |
| 8,679,084 B2 | 3/2014 | Kurihara | |
| 8,758,317 B2 | 6/2014 | Nomoto et al. | |
| 8,764,720 B2 | 7/2014 | Urushihara | |
| 8,795,250 B2 | 8/2014 | O'Connell | |
| 8,853,487 B2 | 10/2014 | Takeuchi et al. | |
| 9,044,356 B2 | 6/2015 | Ng et al. | |
| 9,237,975 B2 | 1/2016 | O'Brien et al. | |
| 10,117,791 B2 | 11/2018 | Iwasaki | |
| 10,238,552 B2 | 3/2019 | Umemoto | |
| 10,376,424 B2 | 8/2019 | Park et al. | |
| 2004/0102756 A1 | 5/2004 | Ichiura et al. | |
| 2005/0080391 A1 | 4/2005 | Yoshimasa et al. | |
| 2008/0294138 A1 | 11/2008 | Andersson et al. | |
| 2009/0054862 A1 | 2/2009 | Tatsukawa | |
| 2009/0306614 A1 | 12/2009 | Boissier | |
| 2009/0306615 A1 | 12/2009 | Olsson | |
| 2011/0046596 A1 | 2/2011 | Kudo et al. | |
| 2012/0046630 A1 | 2/2012 | Kudo et al. | |
| 2012/0089106 A1 | 4/2012 | Komatsu et al. | |
| 2015/0119844 A1* | 4/2015 | Ruman | A61F 13/49413 |
| | | | 604/389 |
| 2017/0246056 A1 | 8/2017 | Tagomori et al. | |
| 2018/0338872 A1 | 11/2018 | Takahashi | |
| 2018/0344544 A1 | 12/2018 | Tally | |
| 2019/0053958 A1 | 2/2019 | Kurihara et al. | |
| 2019/0060139 A1 | 2/2019 | Nagashima | |
| 2019/0269563 A1 | 9/2019 | Yamashita | |
| 2019/0314219 A1 | 10/2019 | Hardie et al. | |
| 2019/0328587 A1 | 10/2019 | Saevecke et al. | |
| 2019/0328588 A1 | 10/2019 | Saevecke et al. | |
| 2019/0343695 A1 | 11/2019 | Ide et al. | |
| 2020/0008988 A1 | 1/2020 | Schmoker et al. | |
| 2020/0030159 A1 | 1/2020 | Ide et al. | |
| 2020/0060888 A1* | 2/2020 | Raycheck | A61F 13/51474 |

FOREIGN PATENT DOCUMENTS

| | | | |
|---|---|---|---|
| CN | 105455960 A | 4/2016 |
| CN | 205379410 U | 7/2016 |
| CN | 106038084 A | 10/2016 |
| CN | 107708636 A | 2/2018 |
| CN | 107874915 A | 4/2018 |
| CN | 107970092 A | 5/2018 |
| CN | 109562002 A | 4/2019 |
| CN | 208877008 U | 5/2019 |
| CN | 107708629 B | 7/2019 |
| CN | 106029024 B | 8/2019 |
| CN | 108463194 B | 8/2019 |
| CN | 106232069 B | 12/2019 |
| CN | 210096090 U | 2/2020 |
| CN | 107072833 B | 4/2020 |
| CN | 111700735 A | 9/2020 |
| CN | 112672721 A | 4/2021 |
| EP | 2285331 B1 | 9/2012 |
| JP | 2011173026 A | 9/2011 |
| KR | 100670558 B1 | 1/2007 |
| WO | 2017169378 A1 | 10/2017 |
| WO | 2019189574 A1 | 10/2019 |
| WO | 2020026684 A1 | 2/2020 |
| WO | 2020059731 A1 | 3/2020 |
| WO | 2020066574 A1 | 4/2020 |

* cited by examiner

ABSORBENT ARTICLE

BACKGROUND OF THE DISCLOSURE

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

Wearers of such conventional absorbent products are interested in having such products demonstrate comfort next to their skin. For many wearers of absorbent articles, the edges of the various materials forming the absorbent articles can cause discomfort to the wearer. For example, the edges of the absorbent core may be felt through the topsheet layer which can cause a feeling of stiffness or abrasiveness to the wearer of the absorbent article.

As a result, there remains a need for an improved product, such as an absorbent article, which has an improved feeling of comfort next to the skin of the wearer. There remains a need for an improved product, such as an absorbent article, which has a reduction in the feeling of stiffness or abrasiveness of the edges of the absorbent core through the topsheet layer of the absorbent article.

SUMMARY OF THE DISCLOSURE

In various embodiments, an absorbent article can have a longitudinal direction, a transverse direction, and a depth direction; a longitudinal direction axis and a transverse direction axis; a first transverse direction end edge and a second transverse direction end edge; an opposing pair of longitudinal direction side edges extending between and connecting the first transverse direction end edge and the second transverse direction end edge; a topsheet layer can have a central layer extending in the longitudinal direction of the absorbent article and symmetrically straddling the longitudinal direction axis, the central layer having a first longitudinal direction side edge and a second longitudinal direction side edge; a first side layer having a first non-folded portion; a first folded portion; and a first inner edge;

wherein the first side layer is in an overlapping configuration with the central layer such that the first inner edge of the first side layer is positioned closer in the transverse direction to the longitudinal centerline than the first longitudinal direction side edge of the central layer and wherein the first side layer does not have a separate elastic material; and a second side layer having a second non-folded portion; a second folded portion; and a second inner edge: wherein the second side layer is in an overlapping configuration with the central layer such that the second inner edge of the second side layer is positioned closer in the transverse direction to the longitudinal centerline than the second longitudinal direction side edge of the central layer and wherein the second side layer does not have a separate elastic material; a backsheet layer; and an absorbent core positioned between the topsheet layer and the backsheet layer and having a first longitudinal direction side edge positioned below the first folded portion of the first side layer and a second longitudinal direction side edge positioned below the second folded portion of the second side layer.

In various embodiments, the first folded portion of the first side layer comprises at least three layers of a material forming the first side layer in an overlapping configuration. In various embodiments, the first folded portion of the first side layer comprises at least four layers of the material forming the first side layer in an overlapping configuration. In various embodiments, the second folded portion of the second side layer comprises at least four layers of a material forming the second side layer in an overlapping configuration. In various embodiments, the second folded portion of the second side layer comprises at least four layers of the material forming the second side layer in an overlapping configuration.

In various embodiments, the first side layer has a first width, measured in the transverse direction, from the first inner edge of the first folded portion of the first side layer and a first bond area between the first side layer and the central layer is from 2 to 20 mm and wherein the second side layer has a second width, measured in the transverse direction, from the second inner edge of the second folded portion of the second side layer and a second bond area between the second side layer and the central layer is from 2 to 20 mm. In various embodiments, the first folded portion of the first side layer has an unattached portion which has a first width in the transverse direction from 3 to 30 mm and wherein the second folded portion of the second side layer has an unattached portion which has a second width in the transverse direction from 3 to 30 mm. In various embodiments, the first folded portion of the first side layer has a first width in the transverse direction between the first inner edge of the first folded portion and a first exterior fold of the first folded portion of greater than 5 mm. In various embodiments, the first folded portion of the first side layer has a first width in the transverse direction between the first inner edge of the first folded portion and the first exterior fold of the first folded portion from 5 mm to 30 mm.

In various embodiments, the second folded portion of the second side layer has a second width in the transverse direction between the second inner edge of the second folded portion and a second exterior fold of the second folded portion of greater than 5 mm. In various embodiments, the second folded portion of the second side layer has a second width in the transverse direction between the second inner edge of the second folded portion and the second exterior fold of the second folded portion from 5 mm to 30 mm.

In various embodiments, the first side layer further comprises a first embossment and wherein the second side layer further comprises a second embossment. In various embodiments, the central layer further comprises a third embossment.

In various embodiments, the absorbent article further has a surge layer.

Figure 1:
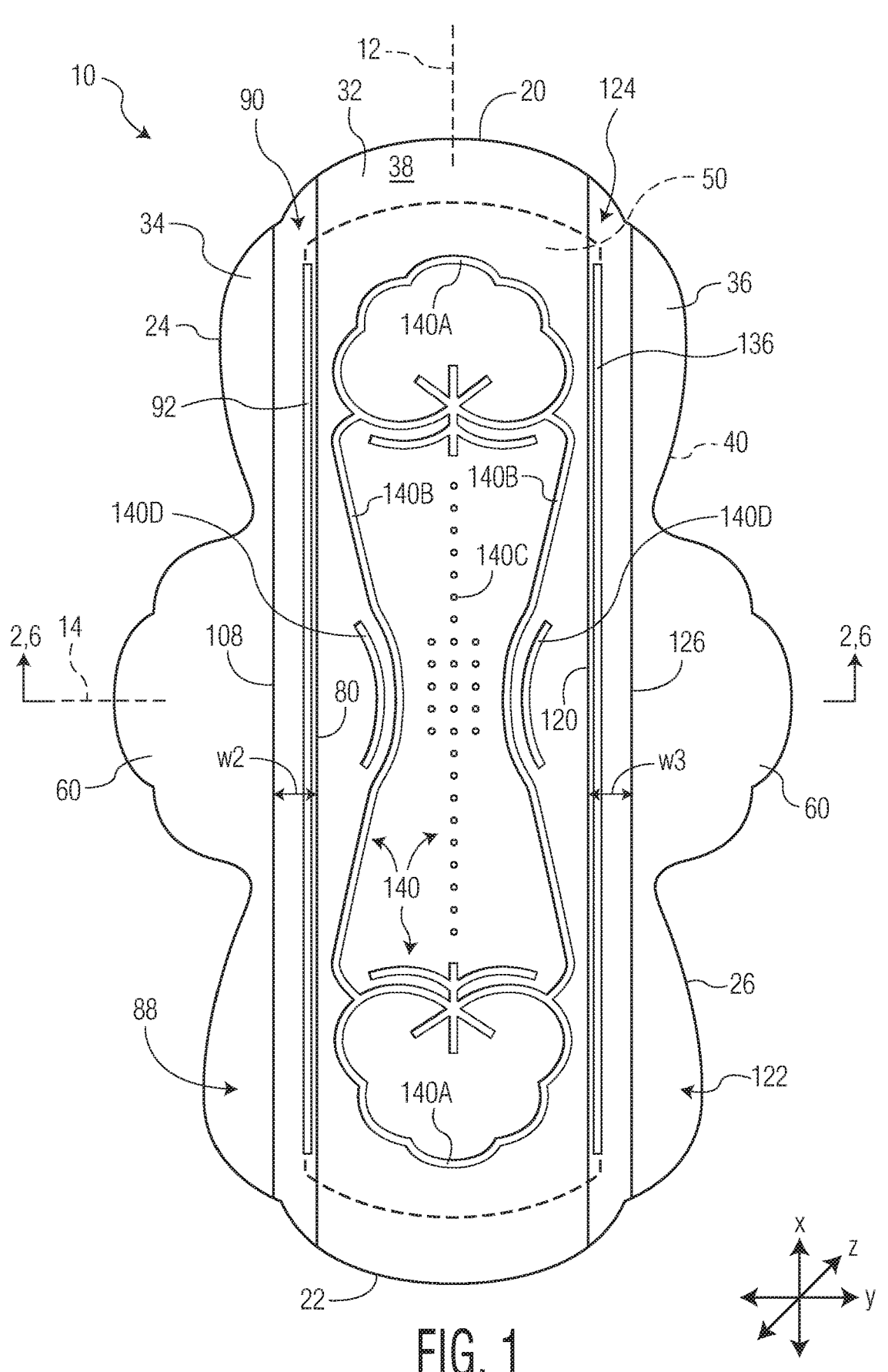
FIG. 1 is a top down view of an embodiment of an absorbent article.

Repeat use of reference characters in the present specification and drawings is intended to represent the same or analogous features or elements of the disclosure.

DETAILED DESCRIPTION OF THE DISCLOSURE

The present disclosure is generally directed towards an absorbent article which can have an improved feeling of comfort next to the skin of the wearer. An absorbent article can have a longitudinal direction, a transverse direction, and a depth direction. The absorbent article can have a topsheet layer, a backsheet layer, and an absorbent core positioned between the topsheet layer and the backsheet layer. The topsheet layer can have a central layer and a pair of side layers. Each of the side layers has a folded portion capable of providing an improved feeling of comfort next to the skin of the wearer.

Definitions

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S.

Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "hydrophilic" refers to surfaces with a water contact angle at or below 59°.

As used herein, the term "hydrophobic" refers to surfaces with the property to repel fluid with a water contact angle at or greater than 90°.

As used herein, the term "semi-hydrophilic" refers to surfaces with a water contact angle from 60° to 89°.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, educative drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethyl-cellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article:

Referring to FIG. 1, FIG. 1 provides an illustration of a top down view of an exemplary absorbent article 10. The absorbent article 10 can have a longitudinal direction (X), a transverse direction (Y), and a depth direction (Z). The absorbent article 10 can have a longitudinal direction axis 12 and a transverse direction axis 14. The absorbent article 10 can have a first transverse direction end edge 20, a second transverse direction end edge 22 opposite the first transverse direction end edge 20, and a pair of opposing longitudinal direction side edges, 24 and 26, extending between and connecting the first transverse direction end edge 20 and the second transverse direction end edge 22. In various embodiments, the absorbent article 10 can take on various geometries but will generally have a pair of opposing longitudinal direction side edges, 24 and 26, and a pair of opposing transverse direction end edges, 20 and 22. The absorbent article 10 can have a wearer facing, liquid permeable topsheet layer 30 which has a central layer 32 and a pair of opposing side layers, 34 and 36. The absorbent article 10 can have a garment facing, liquid impermeable backsheet layer 40. An absorbent core 50 can be positioned between the topsheet layer and the backsheet layer 40.

The topsheet layer 30 and the backsheet layer 40 can both extend beyond the outermost peripheral edges of the absorbent core 50 and can be peripherally bonded together, either entirely or partially, using known bonding techniques to form a sealed peripheral region. For example, the topsheet layer 30 and the backsheet layer 40 can be bonded together by adhesive bonding, ultrasonic bonding, or any other suitable bonding method known in the art.

In various embodiments, the absorbent article 10 can have a pair of wings 60 extending outwardly, in the transverse direction Y, from the absorbent article 10. The wings 60 can drape over the edges of the wearer's undergarment so that the wings 60 are disposed between the edges of the wearer's undergarment and her thighs. The wings 60 can serve at least two purposes. First, the wings 60 can prevent soiling of the wearer's undergarment by forming a barrier along the edges of the undergarment. Second, the wings 60 can be provided with an attachment aid, such as, for example, a garment attachment adhesive or a hook, to keep the absorbent article 10 securely and properly positioned in the undergarment. The wings 60 can wrap around the crotch region of the wearer's undergarment to aid in securing the absorbent article 10 to the wearer's undergarment when in use. Each wing 60 can fold under the crotch region of the wearer's undergarment and the attachment aid can either form a secure attachment to the opposite wing 60 or directly to the surface of the wearer's undergarment. In various embodiments, the wings 60 can be an extension of materials forming the topsheet layer 30 and/or the backsheet layer 40, such that the wings 60 can be of a unitary construction with the absorbent article 10. In various embodiments, the wings 60 can be constructed of materials similar to the topsheet layer 30, the backsheet layer 40 or combinations of these materials. In various embodiments, the wings 60 can be separate elements bonded to the main body of the absorbent article 10. It is to be understood that the wings 60 are optional and, in various embodiments, an absorbent article 10 can be configured without wings 60.

Each of these components of the absorbent article 10, as well as additional components, will be described in more detail herein.

Topsheet Layer:

The topsheet layer 30 defines a wearer facing surface of the absorbent article 10 that may directly contact the body of the wearer and is liquid permeable to receive body exudates. The topsheet layer 30 is desirably provided for comfort and conformability and functions to direct body exudates away from the body of the wearer, through its own structure, and towards the absorbent core 50. The topsheet layer 30 desirably retains little to no liquid in its structure, so that it provides a relatively comfortable and non-irritating surface next to the skin of the wearer of the absorbent article 10. The topsheet layer 30 includes a central layer 32 positioned in an overlapping configuration with first and second opposing side layers, 34 and 36.

The central layer 32 can extend in the longitudinal direction (X) of the absorbent article 10 and can be positioned along and symmetrically straddling the longitudinal direction axis 12 of the absorbent article 10. The central layer 32 can extend between and form a portion of each of the first transverse direction end edge 20 and the second transverse direction end edge 22. The central layer 32 can have a first longitudinal direction side edge 70 and a second longitudinal direction side edge 72 and a width W1 in the transverse direction (T) extending between the first longitudinal direction side edge 70 and the second longitudinal direction side edge 72. In various embodiments, the width W1 between the first longitudinal direction side edge 70 of the central layer 32 and the second longitudinal direction side edge 72 of the central layer 32 can be greater than about 50 mm. In various embodiments, the width W1 between the first longitudinal direction side edge 70 of the central layer 32 and the second longitudinal direction side edge 72 of the central layer 32 can be from about 50 or 60 mm to about 70 or 80 mm.

The central layer 32 can be positioned in an overlapping configuration with each of a first side layer 34 and a second side layer 36. Each of the first side layer 34 and the second side layer 36 can extend in the longitudinal direction (X) of the absorbent article 10. Each of the first side layer 34 and the second side layer 36 can extend the between and form portions of each of the first transverse direction end edge 20 and the second transverse direction end edge 22. To prevent the first longitudinal direction side edge 70 of the central layer 32 from providing any feelings of discomfort or abrasiveness to the wearer of the absorbent article 10, the first side layer 34 is in an overlapping configuration with the first longitudinal direction side edge 70 of the central layer 32 and extends, in the transverse direction (Y) away from the longitudinal direction axis 12, to the first longitudinal direction side edge 24 of the absorbent article 10 where it can form a portion of the first longitudinal direction side edge 24 of the absorbent article 10. Similarly, to prevent the second longitudinal direction side edge 72 of the central layer 32 from providing any feeling of discomfort or abrasiveness to the wearer of the absorbent article 10, the second side layer 36 is in an overlapping configuration with the second longitudinal direction side edge 72 of the central layer 32 and extends, in the transverse direction (Y) away from the longitudinal direction axis 12 and in a direction opposite to the first side layer 34, to the second longitudinal direction side edge 26 of the absorbent article 10 where it can form a portion of the second longitudinal direction side edge 26 of the absorbent article 10.

Each of the first side layer 34 and the second side layer 36 can provide a comfortable feeling to the wearer of the absorbent article 10. In addition to preventing the longitudinal direction side edges, 70 and 72, of the central layer 32 from providing any feeling of discomfort or abrasiveness to the wearer of the absorbent article 10, each of the first side layer 34 and the second side layer 36 can have a folded portion and a non-folded portion. The folded portions, 90 and 124, of each of the first side layer 34 and the second side layer 36, respectively, can provide a multi-layered structure next to the skin of the wearer which can act as a cushion and provide a comfortable feeling to the wearer of the absorbent article 10. In various embodiments, the folded portion of the first side layer comprises at least three layers of a material forming the first side layer in an overlapping configuration. In various embodiments, the folded portion of the first side layer comprises at least four layers of a material forming the first side layer in an overlapping configuration. In various embodiments, the folded portion of the second side layer comprises at least three layers of material forming the second side layer in an overlapping configuration. In various embodiments, the folded portion of the second side layer comprises at least four layers of material forming the second side layer in an overlapping configuration.

Figure 2:
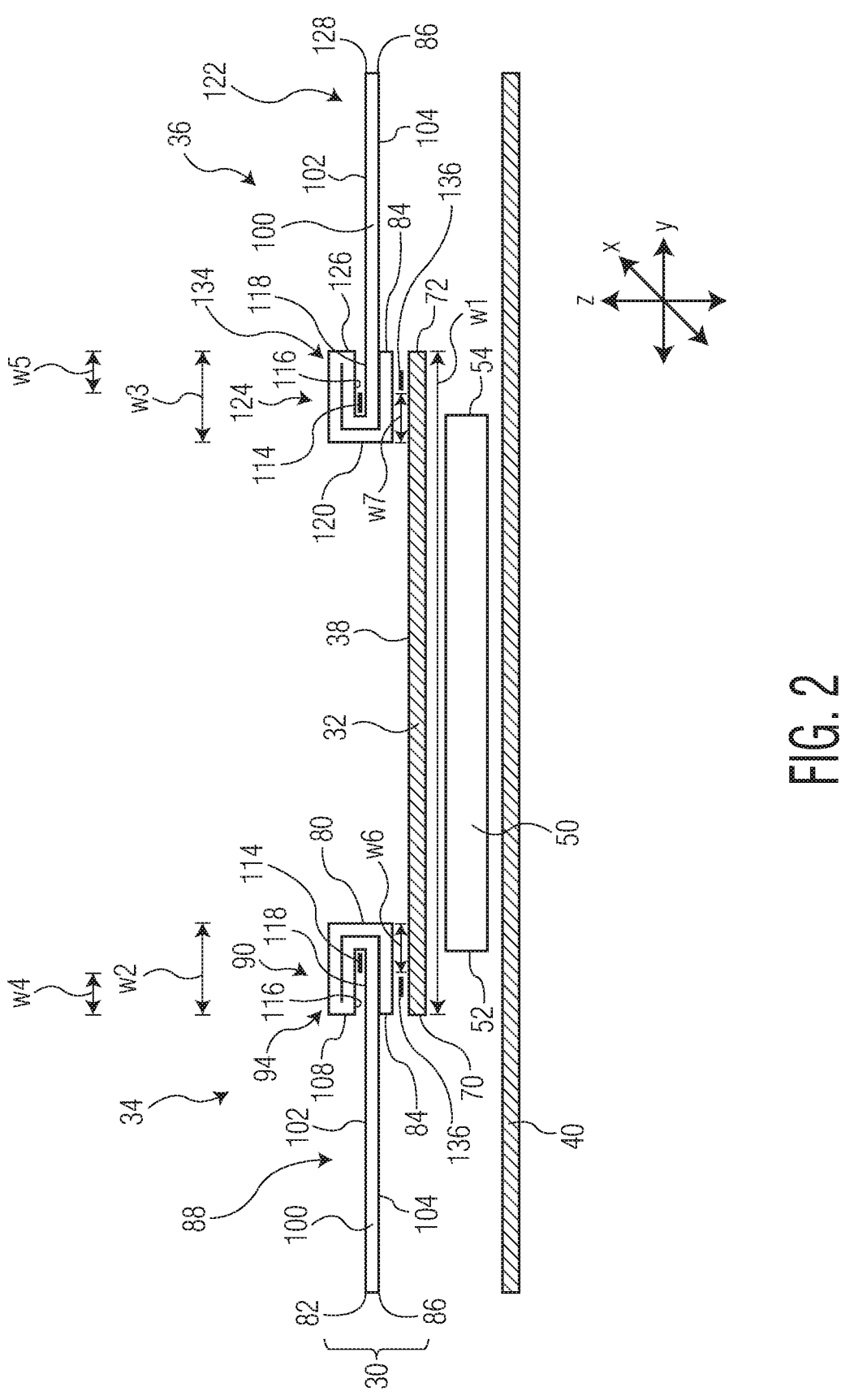
FIG. 2 is an exemplary embodiment of an exploded cross-sectional view of the absorbent article of FIG. 1 taken along line 2-2.
Figure 5:
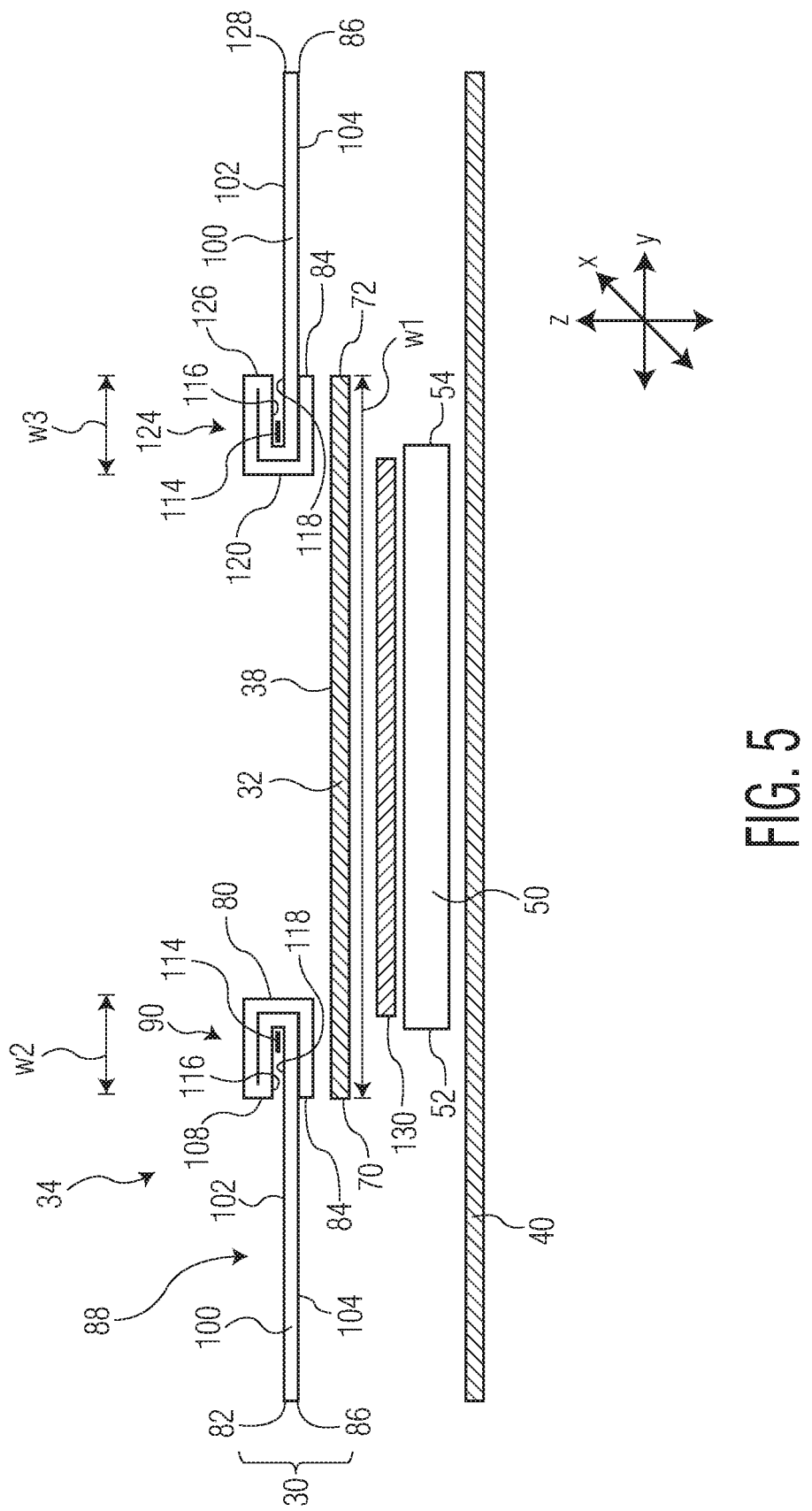
FIG. 5 is an exemplary embodiment of an exploded cross-sectional view of the absorbent article of FIG. 4 taken along line 5-5.

An example of folded portions, 90 and 124, of each of the first side layer 34 and second side layer 36, respectively, can be seen in the exemplary embodiment illustrated in FIGS. 2, 3, and 5. Referring to FIG. 2, the first side layer 34 can be positioned in an overlapping configuration with the central layer 32 such than an inner edge 80 of the first side layer 34 can be positioned between the first longitudinal direction side edge 70 of the central layer 32 and the longitudinal direction axis 12 of the absorbent article 10. Thus, the inner edge 80 of the first side layer 34 is positioned transversely closer to the longitudinal direction axis 12 of the absorbent article 10 than the first longitudinal direction side edge 70 of the central layer 32.

To provide the wearer of the absorbent article 10 with a more comfortable experience when wearing the absorbent article 10, the first side layer 34 has a folded configuration in which a portion of the material 100 forming the first side layer 34 is folded back upon itself resulting in the first side layer 34 having a non-folded portion 88 and a folded portion 90. FIG. 3 provides an exemplary illustration of the folding process placing the material 100 forming the first side layer 34, as illustrated in FIG. 2, into a folded configuration having a non-folded portion 88 and a folded portion 90. In addition to being in an overlapping configuration with the first longitudinal direction side edge 70 of the central layer 32, the folded portion 90 can be positioned in an overlapping configuration with the longitudinal direction side edge 52 of the absorbent core 50 (as well as the longitudinal direction side edges of any other layer of absorbent material present between the topsheet layer 30 and the backsheet layer 40) such that the multiple layers of material forming the folded portion 90 can form a buffer between the longitudinal direction side edge 52 of the absorbent core 50, and any other potential layer between the topsheet layer 30 and the backsheet layer 40, and the body of the wearer and provide a comfortable feeling to the wearer of the absorbent article 10.

Figure 3A:
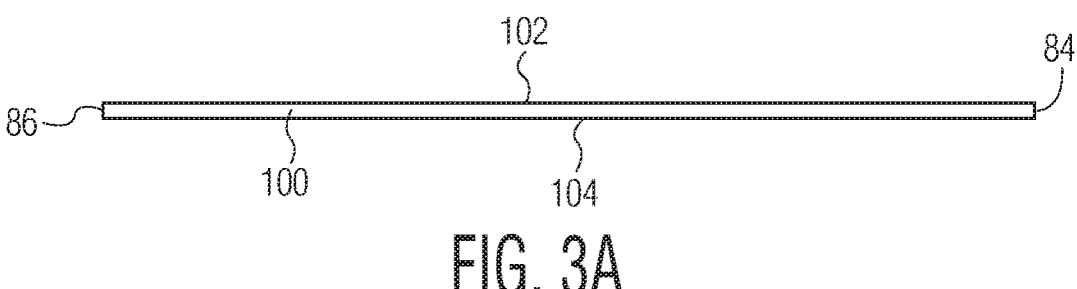
FIGS. 3A-3D are a schematic of a folding process of the material forming a side layer of the topsheet layer illustrated in the exemplary embodiment of FIG. 2.
Figure 3B:
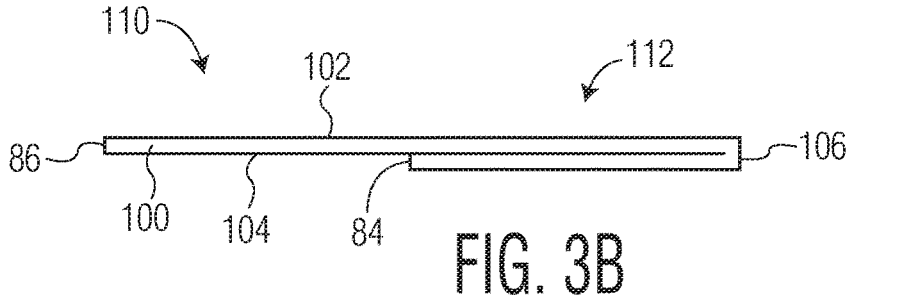
Figure 3C:
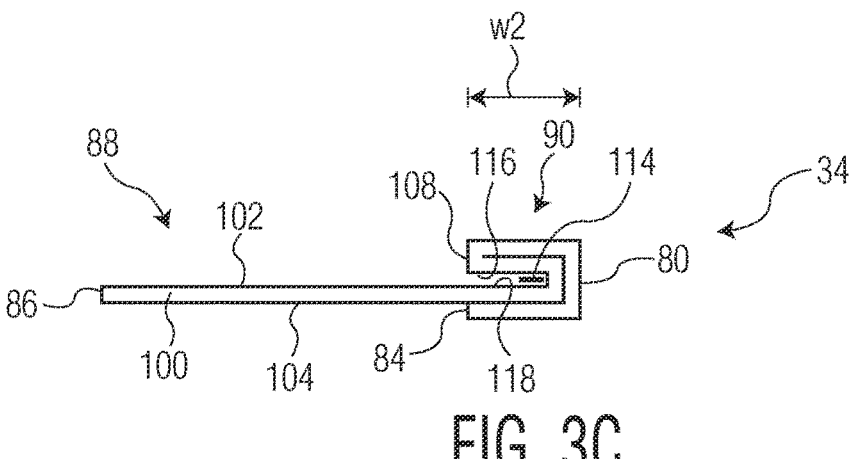
Figure 3D:
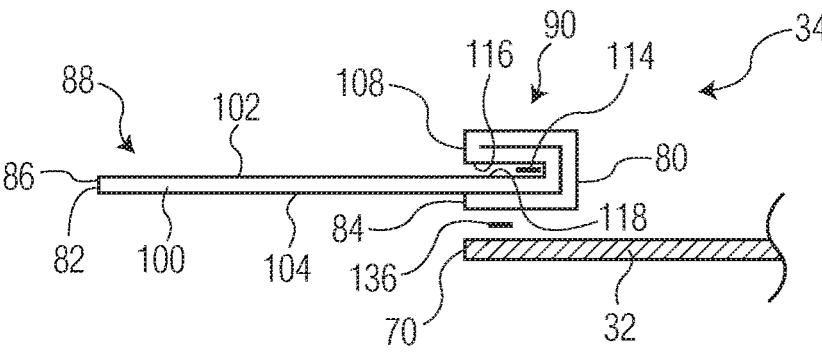

As illustrated in FIG. 3A, the material 100 forming the first side layer 34 has a first major surface 102, a second major surface 104, a first longitudinal direction material edge 84, and a second longitudinal direction material edge 86. In FIG. 3B, a portion of the material 100 is folded downward and back upon itself in order create a first fold 106 (which will ultimately become the exterior fold 108 of the first side layer 34 illustrated in FIG. 2) in the material 100 and to bring a first portion of the second major surface 104 into a facing relationship with a second portion of the second major surface 104. In various embodiments, the first portion of the second major surface 104 and the second portion of the second major surface 104 can be bonded together in order to maintain their facing relationship. Following the process step illustrated in FIG. 3B, the material 100 will have a non-folded region 110 and a folded region 112 in which 2 sections of the material 100 are in an overlapping configuration with each other. The non-folded region 110 of the material 100 will ultimately become the non-folded portion 88 of the first side layer 34 while the folded region 112 of the material 100 will ultimately form the folded portion 90 of the first side layer 34. Referring to FIG. 3C, the folded region 112 is folded, in an upward direction, to bring a first portion of the first major surface 102 into a facing relationship with a second portion of the first major surface 102. The fold formed in FIG. 3C forms the inner edge 80 of the first side layer 34 while the first fold 106 formed in the material 100 becomes the exterior fold 108 of the first side layer 34. In various embodiments, it may be deemed suitable to maintain such a folded configuration and the upper facing surface 116 and the lower facing surface 118 which are in a facing relationship can be bonded together. When a portion of the upper facing surface 116 is bonded to a portion of the lower facing surface 118, a bonded area can be created. For illustrative purposes, in FIGS. 2 and 3B-3D, the bonded area is represented by the location of an adhesive 114 which can be utilized to bond the upper facing layer 116 to the lower facing layer 118. It is to be understood that the upper facing surface 116 and the lower facing surface 118 can be bonded together in any manner deemed suitable such as, for example, utilizing any of the other methods described herein. In various embodiments, the bonded area can be the entirety of the upper facing surface 116 and the lower facing surface 118 which are in a facing relationship. In various embodiments, it may be deemed suitable for less than the entirety of the upper facing surface 116 and the lower facing surface 118 to be. In various embodiments, it may be deemed suitable for the bonded area to be less than 75, 65, 50, 45, 35, or 25% of the surface area forming each of the upper facing surface 116 and the lower facing surface 118. In embodiments in which less than the entirety of the surface area forming each of the upper facing surface 116 and the lower facing surface 118 are bonded together, the reduction in the bonded area begins at the portions of the upper facing surface 116 and lower facing surface 118 which are in the vicinity of the exterior fold 108 of the first side layer 34 and further reductions in the bonded area progressively takes place in a direction towards the inner edge 80 of the first side layer 34. In various embodiments, in which the bonded area is less than the entire entirety of the upper facing surface 116 and the lower facing surface 118, the folded portion 90 can have an unattached portion 94. The unattached portion 94 can contribute to the comfort of the wearer of the absorbent article 10 as there is no bonding present which might increase a feeling of stiffness or inflexibility in the material. The unattached portion 94 can have a width W4, measured in the transverse direction (Y) between the exterior fold 108 of the first side layer 34 and the bonded area, from about 3, 5, 10, 12, 14, 16, or 18 mm to about 20, 22, 24, 26, 28 or 30 mm. As illustrated in FIG. 2, in the folded configuration, the first material side edge 84 of the first side layer 34 is positioned between the inner edge 80 of the first side layer 34 and the first longitudinal direction side edge 24 of the absorbent article 10. Thus, the first material side edge 84 of the first side layer 34 is not co-extensive with the inner edge 80 of the first side layer 34. The first side layer 34 can then be placed into an overlapping configuration with the central layer 32 to form a portion of the topsheet layer 30 of the absorbent article 10. The first side layer 34 can be bonded to the central layer 32 at a bond area. For illustrative purposes, in FIGS. 2 and 3, the bond area is represented by the location of an adhesive 134 which can be utilized to bond the first side layer 34 to the central layer 32. It is to be understood that the first side layer 34 and the central layer 32 can be bonded together in any manner deemed suitable such as, for example, utilizing any of the other methods described herein. In various embodiments, the bond area can be adjacent to the inner edge 80 of the first side layer 34. In various embodiments, the bond area can be spaced apart from the inner edge 80 of the first side layer by a width W6, measured in the transerve direction (Y) between the inner edge 80 and the bond area, by a distance from about 2, 4, 6, 8, or 10 mm to about 12, 14, 16, 18, or 20 mm. The second material side edge 86 is coextensive with the first side layer 34 exterior edge 82. The folded portion 90 of the first side layer 34 can have a width W2 in the transverse direction (Y) extending from the exterior fold 108 of the first side layer 34 to the inner edge 80 of the first side layer. In various embodiments, the width W2 of the folded portion 90 can be uniform in the longitudinal direction (X) of the absorbent article 10. In various embodiments, the width W2 of the folded portion 90 of the first side layer 34 is greater than about 5 mm. In various embodiments, the width W2 of the folded portion 90 of the first side layer 34 is from about 5, 10, 12, 14, 16 or 18 mm to about 20, 22, 24, 26, 28 or 30 mm.

Referring to FIG. 2, the second side layer 36 can be positioned in an overlapping configuration with the central layer 32 such that an inner edge 120 of the second side layer 36 can be positioned between the second longitudinal direction side edge 72 of the central layer 32 and the longitudinal direction axis 12 of the absorbent article 10. Thus, the inner edge 120 of the second side layer 36 is positioned transversely closer to the longitudinal direction axis 12 of the absorbent article 10 than the second longitudinal direction side edge 72 of the central layer 32.

The second side layer 36 can be formed of the same material 100 as the first side layer 34 and can have a first longitudinal direction material edge 84 and a second longitudinal direction material edge 86. Similar to the first side layer 34, to provide the wearer of the absorbent article 10 with a comfortable experience, the second side layer 36 has a folded configuration in which a portion of the material 100 forming the second side layer 36 is folded back upon itself resulting in the second side layer 36 having a non-folded portion 122 and a folded portion 124. FIG. 3 provides an exemplary illustration of the folding process placing the material 100 forming the first side layer 34 into a folded configuration having a non-folded portion 88 and a folded portion 90 and the same process would be followed to place the material 100 forming the second side layer 36 into the folded configuration having a non-folded portion 122 and a folded portion 124. In addition to being in an overlapping configuration with the second longitudinal direction side edge 72 of the central layer 32, the folded portion 124 can be positioned in an overlapping configuration with the longitudinal direction side edge 54 of the absorbent core 50 (as well as the longitudinal direction side edges of any other layer of absorbent material present between the topsheet layer 30 and the backsheet layer 40) such that the multiple layers of material forming the folded portion 124 can form a buffer between the longitudinal direction side edge 54 of the absorbent core 50, and any other potential layer between the topsheet layer 30 and the backsheet layer 40, and the body of the wearer and provide a comfortable feeling to the wearer of the absorbent article 10.

Referring to FIGS. 3A-3D, similar to the first fold of the material forming the first side layer 34, the first fold formed in the material 100 of the second side layer 36 will ultimately become the exterior fold 126 of the second side layer 36. Following FIG. 3B, the material 100 forming the second side layer 36 will have a non-folded region and a folded region in which the non-folded region will ultimately become the non-folded portion 122 of the second side layer 36 while the folded region will ultimately form a portion of the folded portion 124 of the second side layer 36. Similar to folding the material forming the first side layer 34, the fold formed in FIG. 3C forms the inner edge 120 of the second side layer 36 while the first fold formed in the material 100 becomes the exterior fold 126 of the second side layer 36. In various embodiments, it may be deemed suitable to maintain such a folded configuration and the upper facing surface 116 and the lower facing surface 118 which are in a facing relationship can be bonded together. When a portion of the upper facing surface 116 is bonded to a portion of the lower facing surface 118, a bonded area can be created. For illustrative purposes, in FIGS. 2 and 3, the bonded area is represented by the location of an adhesive 114 which can be utilized to bond the upper facing layer 116 to the lower facing layer 118. It is to be understood that the upper facing surface 116 and the lower facing surfaces 118 can be bonded together in any manner deemed suitable such as, for example, utilizing any of the other methods described herein. In various embodiments, the bonded area can be the entirety of the upper facing surface 116 and the lower facing surface 118 which are in a facing relationship. In various embodiments, it may be deemed suitable to coat less than the entirety of the upper facing surface 116 and the lower facing surface 118 to be bonded together. In various embodiments, it may be deemed suitable for the bonded area to be less than 75, 65, 50, 45, 35, or 25% of the surface area forming each of the upper facing surface 116 and the lower facing surface 118. In embodiments in which less than the entirety of the surface area forming each of the upper facing surface 116 and the lower facing surface 118, the reduction in the bonded area begins at the portions of the upper facing surface 116 and lower facing surface 118 which are in the vicinity of the exterior fold 120 of the second side layer 36 and further reductions in the bonded area progressively takes place in a direction towards the inner edge 120 of the second side layer 36. In various embodiments, in which the bonded area is less than the entire entirety of the upper facing surface 116 and the lower facing surface 118, the folded portion 124 can have an unattached portion 134. The unattached portion 134 can contribute to the comfort of the wearer of the absorbent article 10 as there is no bonding present which might increase a feeling of stiffness or inflexibility in the material. The unattached portion 134 can have a width W5, measured in the transverse direction (Y) between the exterior fold 126 of the second side layer 36 and the bonded area, from about 3, 5, 10, 12, 14, 16, or 18 mm to about 20, 22, 24, 26, 28 or 30 mm. As illustrated in FIG. 2, in the folded configuration, the first material side edge 84 of the second side layer 36 is positioned between the inner edge 120 of the second side layer 36 and the second longitudinal direction side edge 26 of the absorbent article 10. Thus, the first material side edge 84 of the second side layer 36 is not co-extensive with the inner edge 120 of the second side layer 36. The second side layer 36 can then be placed into an overlapping configuration with the central layer 32 to form a portion of the topsheet layer 30 of the absorbent article 10. The second side layer 36 can be bonded to the central layer 32 at a bond area. For illustrative purposes, in FIGS. 2 and 3D, the bond area is represented by the location of an adhesive 136 which can be utilized to bond the second side layer 36 to the central layer 32. It is to be understood that the second side layer 36 and the central layer 32 can be bonded together in any manner deemed suitable such as, for example, utilizing any of the other methods described herein. In various embodiments, the bond area can be adjacent to the inner edge 120 of the second side layer 36. In various embodiments, the bond area can be spaced apart from the inner edge 120 of the first side layer by a width W7, measured in the transerve direction (Y) between the inner edge 120 and the bond area, by a distance from about 2, 4, 6, 8, or 10 mm to about 12, 14, 16, 18, or 20 mm. The second material edge 86 is coextensive with the second side layer 36 exterior edge 128. The folded portion 124 of the second side layer 36 can have a width W3 in the transverse direction (Y) extending from the exterior fold 126 of the second side layer 36 to the inner edge 120 of the second side layer 36. In various embodiments, the width W3 of the folded portion 124 can be uniform in the longitudinal direction (X) of the absorbent article 10. In various embodiments, the width W3 of the folded portion 124 of the second side layer 36 is greater than about 5 mm. In various embodiments, the width W3 of the folded portion 124 of the second side layer 36 is from about 5, 10, 12, 14, 16 or 18 mm to about 20, 22, 24, 26, 28, or 30 mm.

Figure 6:
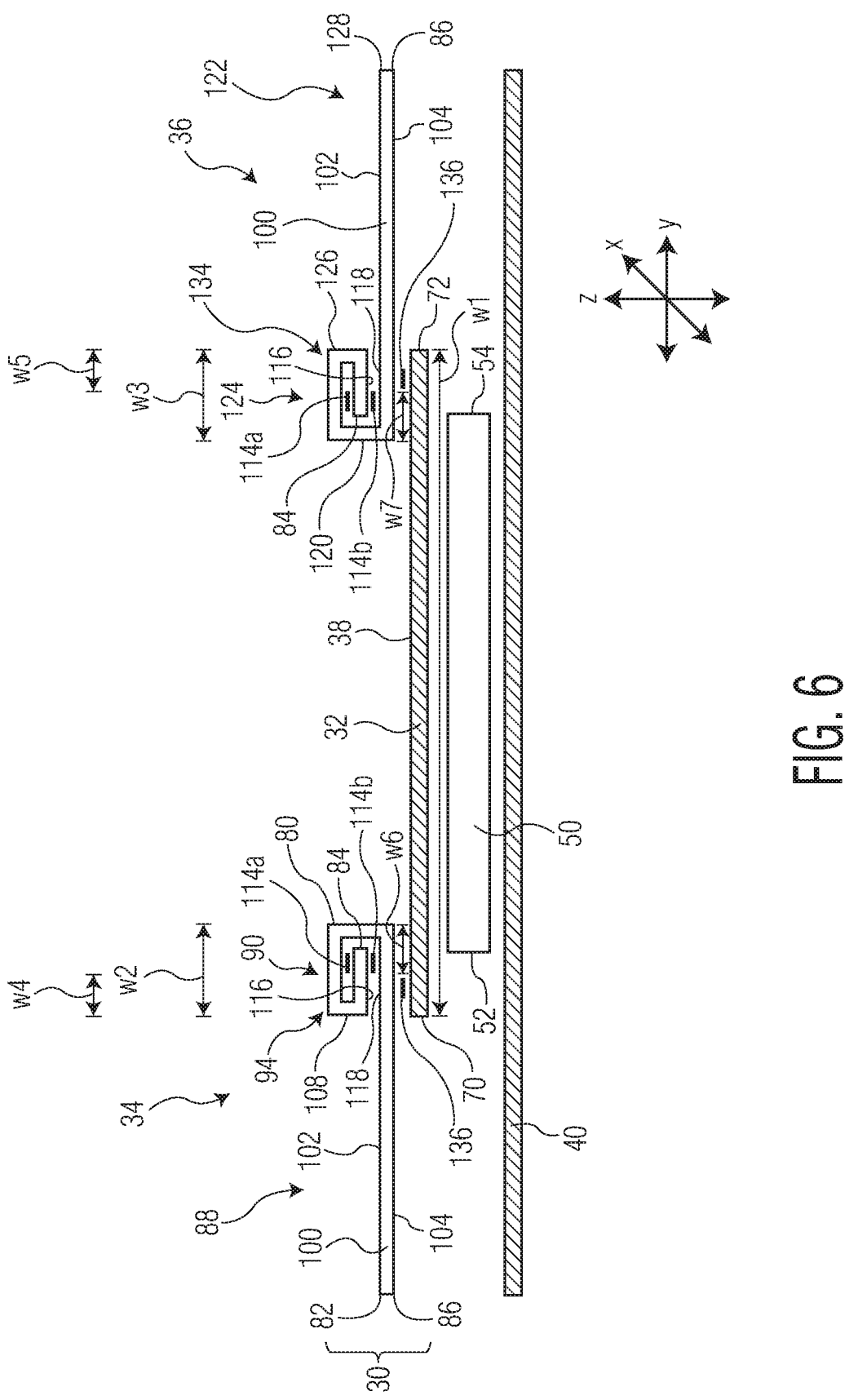
FIG. 6 is an exemplary embodiment of an exploded cross-sectional view of the absorbent article of FIG. 1 taken along line 6-6.
Figure 7A:
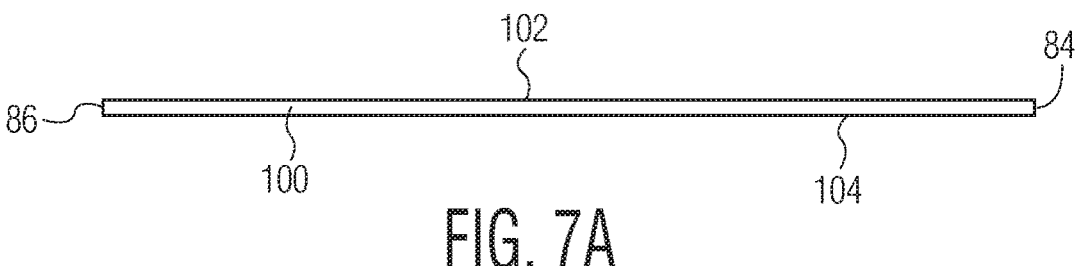
FIGS. 7A-7D are a schematic of a folding process of the material forming a side layer of the topsheet layer illustrated in the exemplary embodiment of FIG. 6.
Figure 7B:
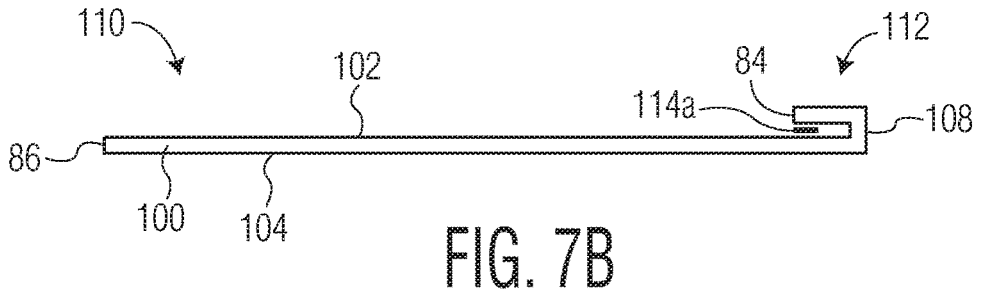
Figure 7C:
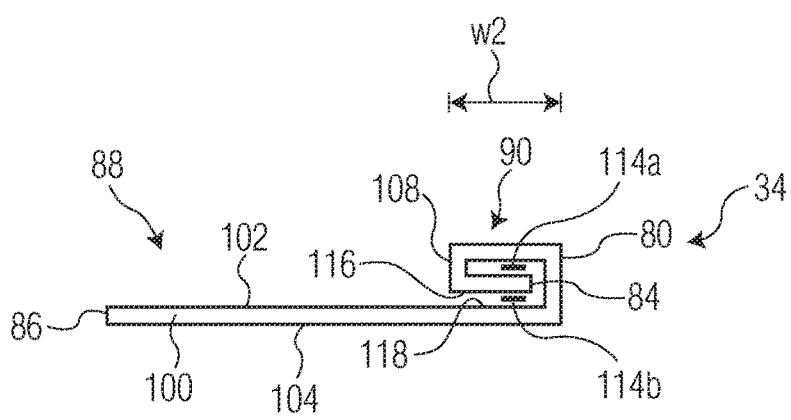
Figure 7D:
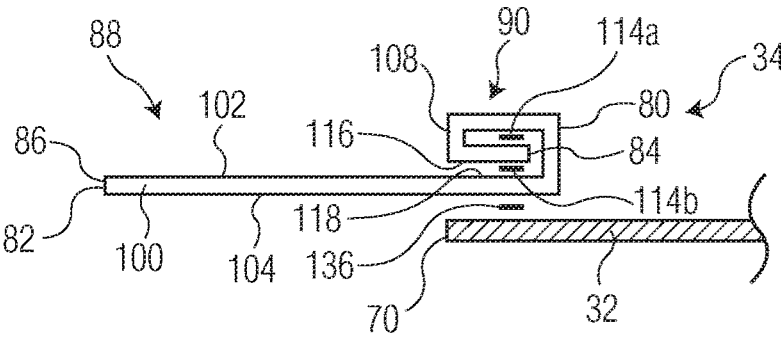
Figure 8:
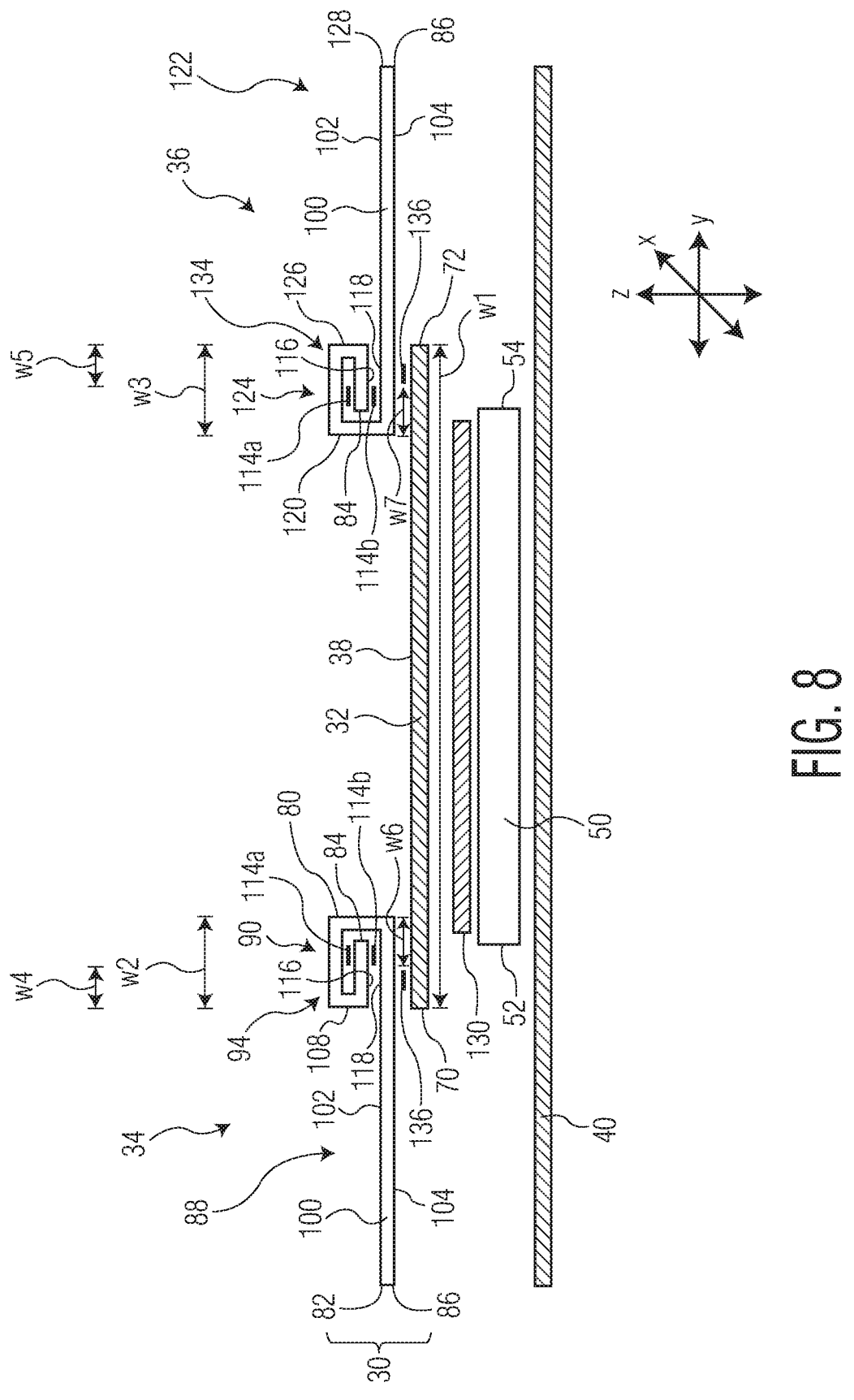
FIG. 8 is an exemplary embodiment of an exploded cross-sectional view of the absorbent article of FIG. 4 taken along line 8-8.

An additional example of folded portions, 90 and 124, of each of the first side layer 34 and second side layer 36, respectively, can be seen in the exemplary embodiment illustrated in FIGS. 6, 7, and 8. Referring to FIG. 6, the first side layer 34 can be positioned in an overlapping configuration with the central layer 32 such than an inner edge 80 of the first side layer 34 can be positioned between the first longitudinal direction side edge 70 of the central layer 32 and the longitudinal direction axis 12 of the absorbent article 10. Thus, the inner edge 80 of the first side layer 34 is positioned transversely closer to the longitudinal direction axis 12 of the absorbent article 10 than the first longitudinal direction side edge 70 of the central layer 32.

To provide the wearer of the absorbent article 10 with a more comfortable experience when wearing the absorbent article 10, the first side layer 34 has a folded configuration in which a portion of the material 100 forming the first side layer 34 is folded back upon itself resulting in the first side layer 34 having a non-folded portion 88 and a folded portion 90. FIG. 7 provides an exemplary illustration of the folding process placing the material 100 forming the first side layer 34, as illustrated in FIG. 6, into a folded configuration having a non-folded portion 88 and a folded portion 90. In addition to being in an overlapping configuration with the first longitudinal direction side edge 70 of the central layer 32, the folded portion 90 can be positioned in an overlapping configuration with the longitudinal direction side edge 52 of the absorbent core 50 (as well as the longitudinal direction side edges of any other layer of absorbent material present between the topsheet layer 30 and the backsheet layer 40) such that the multiple layers of material forming the folded portion 90 can form a buffer between the longitudinal direction side edge 52 of the absorbent core 50, and any other potential layer between the topsheet layer 30 and the backsheet layer 40, and the body of the wearer and provide a comfortable feeling to the wearer of the absorbent article 10.

As illustrated in FIG. 7A, the material 100 forming the first side layer 34 has a first major surface 102, a second major surface 104, a first longitudinal direction material edge 84, and a second longitudinal direction material edge 86. In FIG. 7B, a portion of the material 100 is folded upward and over onto itself in order create a first fold (which will ultimately become the exterior fold 108 of the first side layer 34 illustrated in FIG. 6) in the material 100 and to bring a first portion of the first major surface 102 into a facing relationship with a second portion of the first major surface 102. In various embodiments, the first portion of the first major surface 102 and the second portion of the first major surface 102 can be bonded together in order to maintain their facing relationship. When a portion of the first portion of the first major surface 102 is bonded to a portion of the second portion of the first major surface 102, a bonded area can be created. For illustrative purposes, in FIGS. 6 and 7, the bonded area is represented by the location of an adhesive 114*a* which can be utilized to bond the first portion of the first major surface 102 to the second portion of the first major surface 102. It is to be understood that the first portion of the first major surface 102 and the second portion of the first major surface 102 can be bonded together in any manner deemed suitable such as, for example, utilizing any of the other methods described herein. Following the process step illustrated in FIG. 7B, the material 100 will have a non-folded region 110 and a folded region 112 in which 2 sections of the material 100 are in an overlapping configuration with each other. The non-folded region 110 of the material 100 will ultimately become the non-folded portion 88 of the first side layer 34 while the folded region 112 of the material 100 will ultimately form the folded portion 90 of the first side layer 34. Referring to FIG. 7C, the folded region 112 is folded, again in an upward direction, to bring a first portion of the second major surface 104 into a facing relationship with a third portion of the first major surface 102. The fold formed in FIG. 7C forms the inner edge 80 of the first side layer 34 while the first fold formed in the material 100 becomes the exterior fold 108 of the first side layer 34. In various embodiments, it may be deemed suitable to maintain such a folded configuration and the upper facing surface 116 and the lower facing surface 118 which are in a facing relationship can be bonded together. When a portion of the upper facing surface 116 is bonded to a portion of the lower facing surface 118, a bonded area can be created. For illustrative purposes, in FIGS. 6 and 7, the bonded area is represented by the location of an adhesive 114*b* which can be utilized to bond the upper facing surface 116 to the lower facing surface 118. It is to be understood that the upper facing surface 116 and the lower facing surface 118 can be bonded together in any manner deemed suitable such as, for example, utilizing any of the other methods described herein. In various embodiments, the bonded area can be the entirety of the upper facing surface 116 and the lower facing surface 118 which are in a facing relationship. In various embodiments, it may be deemed suitable for less than the entirety of the upper facing surface 116 and the lower facing surface 118 to be bonded together. In various embodiments, it may be deemed suitable for the bonded area to be less than 75, 65, 50, 45, 35, or 25% of the surface area forming each of the upper facing surface 116 and the lower facing surface 118. In embodiments in which less than the entirety of the surface area forming each of the upper facing surface 116 and the lower facing surface 118 are bonded together, the reduction in the bonded area begins at the portions of the upper facing surface 116 and lower facing surface 118 which are in the vicinity of the exterior fold 108 of the first side layer 34 and further reductions in the bonded area progressively takes place in a direction towards the inner edge 80 of the first side layer 34. In various embodiments, in which the bonded area is less than the entirety of the upper facing surface 116 and the lower facing surface 118, the folded portion 90 can have an unattached portion 94. The unattached portion 94 can contribute to the comfort of the wearer of the absorbent article 10 as there is no bonding present which might increase a feeling of stiffness or inflexibility in the material. The unattached portion 94 can have a width W4, measured in the transverse direction (Y) between the exterior fold 108 of the first side layer 34 and the bonded area, from about 3, 5, 10, 12, 14, 16, or 18 mm to about 20, 22, 24, 26, 28 or 30 mm. As illustrated in FIG. 6, in the folded configuration, the first material side edge 84 of the first side layer 34 is positioned between the inner edge 80 of the first side layer 34 and the first longitudinal direction side edge 24 of the absorbent article 10. Thus, the first material side edge 84 of the first side layer 34 is not co-extensive with the inner edge 80 of the first side layer 34. The first side layer 34 can then be placed into an overlapping configuration with the central layer 32 to form a portion of the topsheet layer 30 of the absorbent article 10. The first side layer 34 can be bonded to the central layer 32 at a bond area. For illustrative purposes, in FIGS. 6 and 7, the bond area is represented by the location of an adhesive 134 which can be utilized to bond the first side layer 34 to the central layer 32. It is to be understood that the first side layer 34 and the central layer 32 can be bonded together in any manner deemed suitable such as, for example, utilizing any of the other methods described herein. In various embodiments, the bond area can be adjacent to the inner edge 80 of the first side layer 34. In various embodiments, the bond area can be spaced apart from the inner edge 80 of the first side layer by a width W6, measured in the transerve direction (Y) between the inner edge 80 and the bond area, by a distance from about 2, 4, 6, 8, or 10 mm to about 12, 14, 16, 18, or 20 mm. The second material side edge 86 is coextensive with the first side layer 34 exterior edge 82. The folded portion 90 of the first side layer 34 can have a width W2 in the transverse direction (Y) extending from the exterior fold 108 of the first side layer 34 to the inner edge 80 of the first side layer. In various embodiments, the width W2 of the folded portion 90 can be uniform in the longitudinal direction (X) of the absorbent article 10. In various embodiments, the width W2 of the folded portion 90 of the first side layer 34 is greater than about 5 mm. In various embodiments, the width W2 of the folded portion 90 of the first side layer 34 is from about 5, 10, 12, 14, 16 or 18 mm to about 20, 22, 24, 26, 28 or 30 mm.

Referring to FIG. 6, the second side layer 36 can be positioned in an overlapping configuration with the central layer 32 such that an inner edge 120 of the second side layer 36 can be positioned between the second longitudinal direction side edge 72 of the central layer 32 and the longitudinal direction axis 12 of the absorbent article 10. Thus, the inner edge 120 of the second side layer 36 is positioned transversely closer to the longitudinal direction axis 12 of the absorbent article 10 than the second longitudinal direction side edge 72 of the central layer 32.

The second side layer 36 can be formed of the same material 100 as the first side layer 34 and can have a first longitudinal direction material edge 84 and a second longitudinal direction material edge 86. Similar to the first side layer 34, to provide the wearer of the absorbent article 10 with a comfortable experience, the second side layer 36 has a folded configuration in which a portion of the material 100 forming the second side layer 36 is folded back upon itself resulting in the second side layer 36 having a non-folded portion 122 and a folded portion 124. FIG. 7 provides an exemplary illustration of the folding process placing the material 100 forming the first side layer 34 into a folded configuration having a non-folded portion 88 and a folded portion 90 and the same process would be followed to place the material 100 forming the second side layer 36 into the folded configuration having a non-folded portion 122 and a folded portion 124. In addition to being in an overlapping configuration with the second longitudinal direction side edge 72 of the central layer 32, the folded portion 124 can be positioned in an overlapping configuration with the longitudinal direction side edge 54 of the absorbent core 50 (as well as the longitudinal direction side edges of any other layer of absorbent material present between the topsheet layer 30 and the backsheet layer 40) such that the multiple layers of material forming the folded portion 124 can form a buffer between the longitudinal direction side edge 54 of the absorbent core 50, and any other potential layer between the topsheet layer 30 and the backsheet layer 40, and the body of the wearer and provide a comfortable feeling to the wearer of the absorbent article 10.

Referring to FIG. 7, similar to the first fold of the material forming the first side layer 34, the first fold formed in the material 100 of the second side layer 36 will ultimately become the exterior fold 126 of the second side layer 36. Following the process step illustrated in FIG. 7B, the material 100 forming the second side layer 36 will have a non-folded region and a folded region in which the non-folded region will ultimately become the non-folded portion 122 of the second side layer 36 while the folded region will ultimately form a portion of the folded portion 124 of the second side layer 36. Similar to folding the material forming the first side layer 34, the fold formed in FIG. 7C forms the inner edge 120 of the second side layer 36 while the first fold formed in the material 100 becomes the exterior fold 126 of the second side layer 36. In various embodiments, it may be deemed suitable to maintain such a folded configuration and the upper facing surface 116 and the lower facing surface 118 which are in a facing relationship can be bonded together. When a portion of the upper facing surface 116 is bonded to a portion of the lower facing surface 118, a bonded area can be created. For illustrative purposes, in FIGS. 6 and 7, the bonded area is represented by the location of an adhesive 114b which can be utilized to bond the upper facing layer 116 to the lower facing layer 118. It is to be understood that the upper facing surface 116 and the lower facing surfaces 118 can be bonded together in any manner deemed suitable such as, for example, utilizing any of the other methods described herein. In various embodiments, the bonded area can be the entirety of the upper facing surface 116 and the lower facing surface 118 which are in a facing relationship. In various embodiments, it may be deemed suitable to coat less than the entirety of the upper facing surface 116 and the lower facing surface 118 to be bonded together. In various embodiments, it may be deemed suitable for the bonded area to be less than 75, 65, 50, 45, 35, or 25% of the surface area forming each of the upper facing surface 116 and the lower facing surface 118. In embodiments in which less than the entirety of the surface area forming each of the upper facing surface 116 and the lower facing surface 118 are bonded together, the reduction in the bonded area begins at the portions of the upper facing surface 116 and lower facing surface 118 which are in the vicinity of the exterior fold 120 of the second side layer 36 and further reductions in the bonded area progressively takes place in a direction towards the inner edge 120 of the second side layer 36. In various embodiments, in which the bonded area is less than the entirety of the upper facing surface 116 and the lower facing surface 118, the folded portion 124 can have an unattached portion 134. The unattached portion 134 can contribute to the comfort of the wearer of the absorbent article 10 as there is no bonding present which might increase a feeling of stiffness or inflexibility in the material. The unattached portion 134 can have a width W5, measured in the transverse direction (Y) between the exterior fold 126 of the second side layer 36 and the bonded area, from about 3, 5, 10, 12, 14, 16, or 18 mm to about 20, 22, 24, 26, 28 or 30 mm. As illustrated in FIG. 6, in the folded configuration, the first material side edge 84 of the second side layer 36 is positioned between the inner edge 120 of the second side layer 36 and the second longitudinal direction side edge 26 of the absorbent article 10. Thus, the first material side edge 84 of the second side layer 36 is not co-extensive with the inner edge 120 of the second side layer 36. The second side layer 36 can then be placed into an overlapping configuration with the central layer 32 to form a portion of the topsheet layer 30 of the absorbent article 10. The second side layer 36 can be bonded to the central layer 32 at a bond area. For illustrative purposes, in FIGS. 6 and 7D, the bond area is represented by the location of an adhesive 136 which can be utilized to bond the second side layer 36 to the central layer 32. It is to be understood that the second side layer 36 and the central layer 32 can be bonded together in any manner deemed suitable such as, for example, utilizing any of the other methods described herein. In various embodiments, the bond area can be adjacent to the inner edge 120 of the second side layer 36. In various embodiments, the bond area can be spaced apart from the inner edge 120 of the first side layer by a width W7, measured in the transerve direction (Y) between the inner edge 120 and the bond area, by a distance from about 2, 4, 6, 8, or 10 mm to about 12, 14, 16, 18, or 20 mm. The second material edge 86 is coextensive with the second side layer 36 exterior edge 128. The folded portion 124 of the second side layer 36 can have a width W3 in the transverse direction (Y) extending from the exterior fold 126 of the second side layer 36 to the inner edge 120 of the second side layer 36. In various embodiments, the width W3 of the folded portion 124 can be uniform in the longitudinal direction (X) of the absorbent article 10. In various embodiments, the width W3 of the folded portion 124 of the second side layer 36 is greater than about 5 mm. In various embodiments, the width W3 of the folded portion 124 of the second side layer 36 is from about 5, 10, 12, 14, 16 or 18 mm to about 20, 22, 24, 26, 28, or 30 mm.

In various embodiments, each of the first side layer 34 and the second side layer 36 can be provided with an embossment 92 respectively. The embossments 92 can be incorporated into the first side layer 34 and the second side layer 36, respectively, via any known embossing technique. The embossments 92 can be incorporated into the first side layer 34 and second side layer 36 prior to, while, or after bonding each side layer, 34 and 36, to the central layer 32 to form the topsheet layer 30. An embossment can be configured in any aesthetically pleasing pattern and can be a continuous embossment or a discrete embossment. For example, as illustrated in FIG. 1, each embossment 92 is a continuous rectangular shape extending generally in the longitudinal direction (X) of the absorbent article 10 and extending the majority of the overall length, in the longitudinal direction (X) of the absorbent article 10. In various embodiments, an embossment can be a discrete element such as, for example, but not limited to, circle, oval, square, rectangle, diamond, star, flower, or any other shape deemed suitable. An emboss-ment can have any length in the longitudinal direction (X) and any width in the transverse direction (Y) as deemed suitable.

The central layer 32 of the topsheet layer 30 can be constructed of any woven, nonwoven, or film sheet material which is easily penetrated by bodily exudates which may contact the body-facing surface 38 of the central layer 32. In various embodiments, the central layer 32 can be con-structed from various nonwoven webs such as meltblown webs, spunlace webs, spunbond webs, hydroentangled spun-lace webs, or through air bonded carded webs. Examples of suitable central layer 32 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density poly-ethylene, and aliphatic esters such as polylactic acid. Finely perforated films and net materials can also be used, as can laminates of/or combinations of these materials. An example of a suitable central layer 32 can be a cotton spunlace material. An example of a material suitable for use as a central layer 32 is a perforated polyethylene film material. An example of a suitable central layer 32 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other materials that may be used as the central layer 32, each of which is hereby incorporated by reference thereto in its entirety. Additional central layer 32 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the central layer 32 may contain a plurality of apertures formed therethrough to permit body exudates to pass more readily into the absorbent core 50. The apertures may be randomly or uniformly arranged through-out the central layer 32 of the topsheet layer 30 or they may be located in a narrow longitudinal band or strip arranged along the longitudinal direction axis 12 of the absorbent article 10. The size, shape, diameter, and number of aper-tures may be varied to suit an absorbent article's 10 par-ticular needs.

In various embodiments, the central layer 32 can have a basis weight ranging from about 5, 10, 15, 20 or 25 gsm to about 50, 100, 120, 125 or 150 gsm. For example, in an embodiment, a central layer 32 can be constructed from a through air bonded carded web having a basis weight ranging from about 15 gsm to about 100 gsm. In another example, a central layer 32 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others. Alternatively, aper-tured films, such as those available from such film suppliers as Texol, Italy and Tredegar, U.S.A. may be utilized. In various embodiments, the central layer 32 can be con-structed from a perforated polyethylene film having a basis weight from about 15 gsm to about 30 gsm. In various embodiments, the central layer 32 can be constructed from a cotton material and have a basis weight from about 25 gsm to about 35 gsm.

In various embodiments, the central layer 32 of the topsheet layer 30 is hydrophilic and has a water contact angle of less than 59°. The central layer 32 can be formed from a material which is inherently hydrophilic or can be formed from a hydrophobic material which has then been treated with a hydrophilic coating such as, for example, a surfactant treatment.

Each of the first side layer 34 and the second side layer 36 can be constructed of any woven, nonwoven, or film sheet materials that can be the same as or different from the material selected to form the central layer 32 of the topsheet layer 30. The selection of the particular materials for form-ing the first side layer 34 and the second side layer 36 can vary based upon the overall desired attributes of the first side layer 34 and the second side layer 36. For example, it may be desired to have a hydrophilic material forming the central layer 32 and semi-hydrophilic barrier type materials forming each of the first side layer 34 and the second side layer 36 to prevent leakage and increase a sense of dryness in the area of each of the first side layer 34 and the second side layer 36. For example, various nonwoven fabrics or webs such as meltblown webs, spunbond webs, or through-air bonded carded webs (TABCW) can be utilized to form each of the first side layer 34 and the second side layer 36. In various embodiments, each of the first side layer 34 and the second side layer 36 have semi-hydrophilic barrier properties in which the materials forming the first side layer 34 and the second side layer 36 each have a water contact angle from 60° or 70° to 80° or 89°. To avoid discomfort to the wearer of the absorbent article 10, in various embodiments, each of the first side layer 34 and the second side layer 36 do not have a separate elastic material incorporated therein. A separate elastic material, such as, for example, an elastic strand or ribbon, may cause undue tension against the skin of the wearer of the absorbent article 10 which may result in pinched skin or red markings.

In various embodiments, each of the first side layer 34 and the second side layer 36 can be bonded to the central layer 32 utilizing an adhesive. In various embodiments, each of the first side layer 34 and the second side layer 36 can be bonded to the central layer 32 utilizing an embossing technique. In various embodiments, in additional to utilizing an embossing technique, each of the first side layer 34 and the second side layer 36 can also be adhesively, thermally, or ultrasonically, bonded to the central layer 32. Traditional absorbent article construction adhesive may be used to bond the first side layer 34 and the second side layer 36 the central layer 32. Either of the central layer 32 and/or the first or second side layers, 34 and/or 36, may be treated with surfactants and/or skin-health benefit agents, as are well known in the art.

Such longitudinally directed first side layer 34 and second side layer 36 can be of a single or multi-layered construc-tion. In various embodiments, the first side layer 34 and the second side layer 36 are formed from a single layer con-struction. In various embodiments, the first side layer 34 and the second side layer 36 are formed from combining a mixture of hydrophilic and hydrophobic fibers together. For example, in various embodiments, the first side layer 34 and the second side layer 36 can be formed by combining 30% hydrophobic fibers and 70% hydrophilic fibers together and forming a TABCW material. In various embodiments, the first side layer 34 and the second side layer 36 can be formed by combining 50% hydrophobic fibers and 50% hydrophilic fibers together and forming a TABCW material. In various embodiments, the first side layer 34 and the second side layer 36 can be adhesively or otherwise bonded laminates. In various embodiments, the first side layer 34 and the second side layer 36 can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. The film layer may also serve as a barrier layer to prevent rewet of the first side layer 34 and the second side layer 36 as well as to prevent the flow of fluid off the side edges of the absorbent article 10. In various embodiments, the first side layer 34 and the second side layer 36 can be laminates such as a spunbond-meltblown-meltblown-spunbond layer ("SMMS") laminate, spunbond-film laminate, or alternatively, other nonwoven laminate combinations.

Absorbent Core:

An absorbent core 50 can be positioned between the topsheet layer 30 and the backsheet layer 40. The absorbent core 50 can generally be any single layer structure or combination of layer components, which can demonstrate some level of compressibility, conformability, be non-irritating to a wearer's skin, and capable of absorbing and retaining liquids and other body exudates. Additionally, the absorbent core 50 can provide additional capacity to absorb and retain body exudates such as menses. In various embodiments, the absorbent core 50 can be formed from a variety of different materials and can contain any number of desired layers. For example, the absorbent core 50 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 50 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and $\alpha$-olefins, poly(vinyl pyrrolidone), poly (vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 50 in any amount as desired.

Regardless of the combination of absorbent materials used in the absorbent core 50, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 50 can vary as desired and can comprise any one of various shapes including, but not limited to, triangular, rectangular, dog-bone and elliptical shapes. In various embodiments, the absorbent core 50 can have a shape that generally corresponds with the overall shape of the absorbent article 10. The dimensions of the absorbent core 50 can be substantially similar to those of the absorbent article 10, however, it will be appreciated that the dimensions of the absorbent core 50 while similar, will often be less than those of the overall absorbent article 10, in order to be adequately contained therein.

By way of example, suitable materials and/or structures for the absorbent core 50 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 50 can be a single layer structure and can include, for example, a matrix of cellulosic fluff and superabsorbent material. In various embodiments, an absorbent core 50 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 50 may be constructed of an airlaid material and the garment facing layer of the absorbent core 50 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Embossing:

In various embodiments, the absorbent article 10 may have embossments incorporated therein which can provide topography to the absorbent article 10 as well as an aesthetically pleasing appearance. The embossments can be configured in any aesthetically pleasing pattern, can be positioned symmetrically, or can be positioned asymmetrically within the absorbent article 10. An embossment can be provided with any shape and configuration as deemed suitable. For example, an embossment can be in the shape of a circle, oval, square, rectangle, diamond, or any other geometric shape deemed suitable. An embossment can have any length in the longitudinal direction (X) as deemed suitable and a width in the transverse direction (Y) as deemed suitable.

Suitable embossing techniques include, for example, the use of raised elements to impart the desired embossing pattern to create a compression, an embossment, in the layers of the absorbent article 10. For instance, a suitable process may include using thermal bonding wherein the absorbent article 10 is passed through two rolls (e.g., steel, rubber, etc.) where one is engraved with an embossing pattern and the other is flat. One or both rolls may be heated. In addition, thermal and/or ultrasonic bonding techniques may be employed to create the embossing regions.

Figure 4:
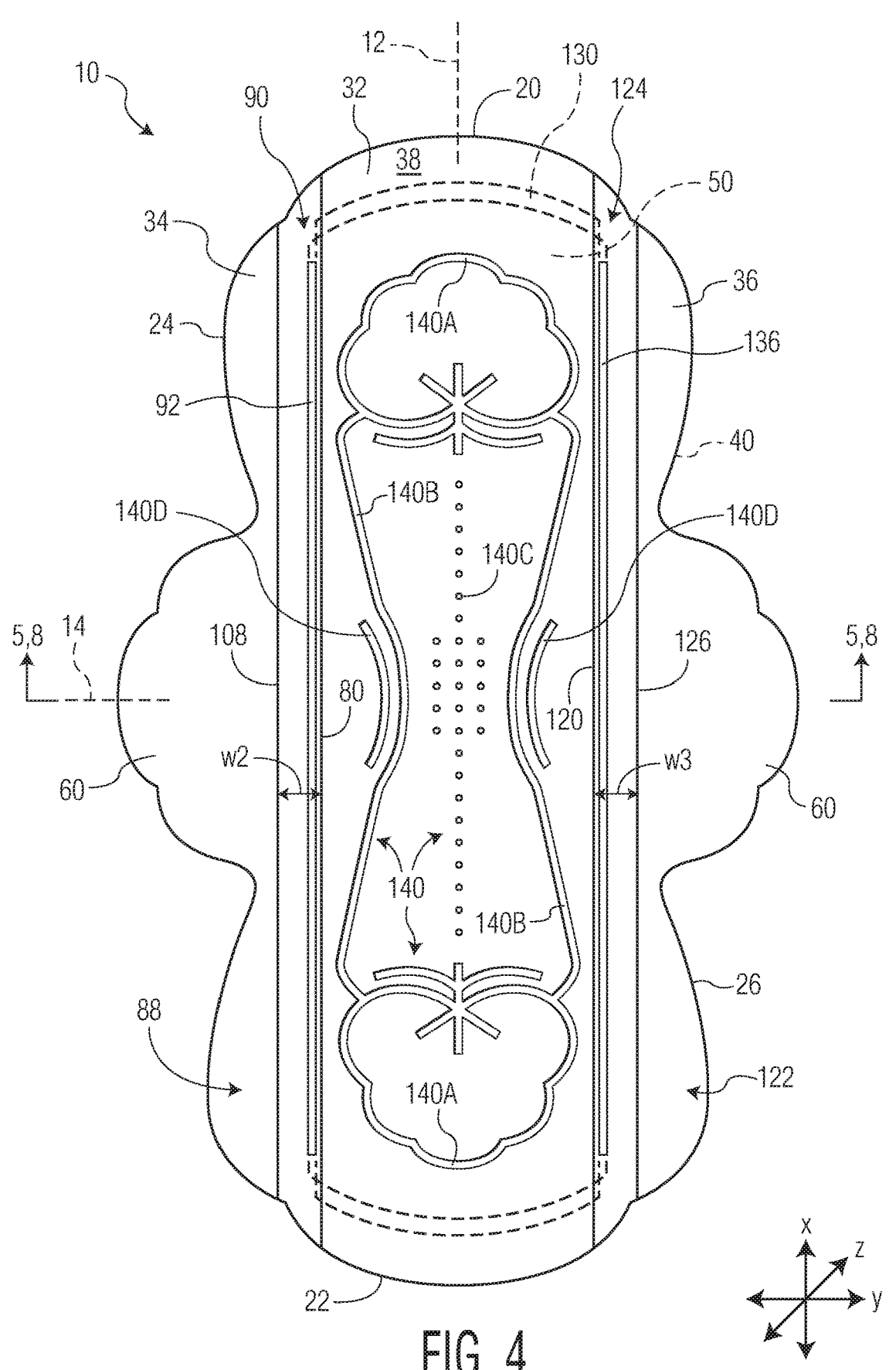
FIG. 4 is a top down view of an embodiment of an absorbent article.

Referring to FIG. 1, in addition to the embossments 92 present in the first side layer 34 and the second side layer 36, respectively, the absorbent article 10 has additional emboss- ments 140 incorporated over the central layer 32 of the topsheet layer 30 which can extend in the depth direction (Z) into at least the absorbent core 50 and, in various embodi- ments, into other layers of material, if present, such as, for example, a surge layer (as illustrated in FIG. 4). The embossments 140 illustrated in FIG. 1 provide the wearer of the absorbent article 10 with a visual image of cotton embossments 140A at each end of the absorbent article which are connected via generally angled geometric embossments 140B. The cotton embossments 140A may signal to the wearer that the absorbent article 10 contains particular materials such as cotton materials. Contained within the generally geometric embossments 140B are cir- cular pinpoint embossments 140C which can help the wearer identify the primary body exudate capture region of the absorbent article 10 for proper placement of the absorbent article 10 within their underwear. Additional embossments, such as the arcuate embossments 140D can further reinforce for the wearer of the absorbent article 10 the primary body exudate capture region of the absorbent article 10 for proper placement of the absorbent article 10 in their underwear.

Backsheet Layer:

The backsheet layer 40 is generally liquid impermeable and is the portion of the absorbent article 10 which faces the garment of the wearer. The backsheet layer 40 can permit the passage of air or vapor out of the absorbent article 10 while still blocking the passage of liquids. Any liquid impermeable material may generally be utilized to form the backsheet layer 40. The backsheet layer 40 can be composed of a single layer or multiple layers, and these one or more layers can themselves comprise similar or different materials. Suitable material that may be utilized can be a microporous poly- meric film, such as a polyolefin film of polyethylene or polypropylene, nonwovens and nonwoven laminates, and film/nonwoven laminates. The particular structure and com- position of the backsheet layer 40 can be selected from various known films and/or fabrics with the particular mate- rial being selected as appropriate to provide the desired level of liquid barrier, strength, abrasion resistance, tactile prop- erties, aesthetics and so forth. In various embodiments, a polyethylene film can be utilized that can have a thickness in the range of from about 0.2 or 0.5 mils to about 3.0 or 5.0 mils. An example of a backsheet layer 40 can be a polyeth- ylene film such as that obtainable from Pliant Corporation, Schaumburg, IL, USA. Another example can include cal- cium carbonate-filled polypropylene film. In still another embodiment, the backsheet layer 40 can be a hydrophobic nonwoven material with water barrier properties such as a nonwoven laminate, an example of which can be a spun- bond, meltblown, meltblown, spunbond, four-layered lami- nate. The backsheet layer 40 can, therefore, be of a single or multiple layer construction, such as of multiple film layers or laminates of film and nonwoven fibrous layers. Suitable backsheet layers 40 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Surge Layer:

Referring to FIGS. 4, 5, and 8, in various embodiments, an additional layer in the absorbent article 10 can be a surge layer 130. A surge layer 130 can be constructed of any woven or nonwoven material that is easily penetrated by body exudates. The surge layer 130 can help to absorb, decelerate, and diffuse surges or gushes of liquid that may be rapidly introduced into the absorbent article 10. The surge layer 130 can rapidly accept and temporarily hold the liquid prior to releasing the liquid into the absorbent core 50. Various woven fabrics and nonwoven webs can be used to construct the surge layer 130. For example, the surge layer 130 can comprise a nonwoven fabric layer composed of a meltblown or spunbond web of polyolefin or polyester filaments. Such nonwoven fabric layers may include conju- gate, biconstituent and homopolymer fibers of staple or other lengths and mixtures of such fibers with other types of fibers. The surge layer 130 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layer 130 typically has a basis weight of less than about 100 gsm, and in some embodiments, from about 10 gsm to about 40 gsm.

The surge layer 130 can be incorporated into the absor- bent article 10 in any suitable size and shape based upon the need of the particular absorbent article 10 in which the surge layer 130 is being used. In various embodiments, the surge layer 130 can extend across the entire absorbent article 10 in the longitudinal direction and transverse direction, such that the surge layer 130 can have the same dimensions as the topsheet layer 30. In various embodiments, the surge layer 130 can have a smaller overall length in the longitudinal direction and a smaller overall width in the transverse direction than the topsheet layer 30. In various embodi- ments, the overall length of the surge layer 130 can be from about 30, 40 or 50% to about 98, 99 or 100% of the overall length of the topsheet layer 30. In various embodiments, the overall width of the surge layer 130 can be from about 10, 25 or 50% to about 98, 99 or 100% of the overall width of the topsheet layer 30.

Wings:

The wings 60 can be constructed from materials described above with respect to the topsheet layer 30 and the backsheet layer 40. In various embodiments, the wings 60 can com- prise an extension of a layer of material within the topsheet layer 30 and/or the backsheet layer 40. By way of example, the wings 60 can be formed by an extension of the topsheet layer 30 and backsheet layer 40 that are then bonded together along peripheral seal. Such wings 60 can be inte- grally formed with the main portion of the absorbent article 10. Alternatively, the wings 60 can be formed independently and separately attached to an intermediate section of the absorbent article 10. Wings 60 that are made independent of the other components of the absorbent article 10 can be bonded to a portion of the topsheet layer 30 and/or backsheet layer 40. Examples of processes for manufacturing absorbent articles 10 and wings 60 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article characterized by comprising:
   a. a longitudinal direction, a transverse direction, and a depth direction;
   b. a longitudinal direction axis and a transverse direction axis;
   c. a first transverse direction end edge and a second transverse direction end edge;
   d. an opposing pair of longitudinal direction side edges extending between and connecting the first transverse direction end edge and the second transverse direction end edge;
   e. a topsheet layer comprising:
      i. a central layer extending in the longitudinal direction of the absorbent article and symmetrically straddling the longitudinal direction axis, the central layer having a first longitudinal direction side edge and a second longitudinal direction side edge;
      ii. a first side layer comprising:
         1. A first non-folded portion;
         2. a first folded portion; and
         3. A first inner edge;
         4. wherein the first side layer is in an overlapping configuration with the central layer such that the first inner edge of the first side layer is positioned closer in the transverse direction to the longitudinal centerline than the first longitudinal direction side edge of the central layer and wherein the first side layer does not have a separate elastic material;
         5. Wherein the first side layer comprises a first material comprised of one or more layers and wherein the first folded portion of the first side layer comprises a first fold of the first side layer such that the folded portion of the first side layer comprises at least three layers of the first material forming the first side layer in an overlapping configuration; and
      iii. a second side layer comprising:
         1. A second non-folded portion;
         2. a second folded portion; and
         3. A second inner edge;
         4. wherein the second side layer is in an overlapping configuration with the central layer such that the second inner edge of the second side layer is positioned closer in the transverse direction to the longitudinal centerline than the second longitudinal direction side edge of the central layer and wherein the second side layer does not have a separate elastic material;
         5. Wherein the second side layer comprises a second material having one or more layers and wherein the second folded portion of the second side layer comprises a first fold of the second folded portion such that the folded portion of the second side layer comprises at least three layers of the second material forming the second side layer in an overlapping configuration; and
   f. a backsheet layer; and
   g. an absorbent core positioned between the topsheet layer and the backsheet layer and having a first longitudinal direction side edge positioned below the first folded portion of the first side layer and a second longitudinal direction side edge positioned below the second folded portion of the second side layer.

2. The absorbent article of claim 1 wherein the first folded portion of the first side layer comprises at least four layers of the first material forming the first side layer in an overlapping configuration.

3. The absorbent article of claim 1 wherein the second folded portion of the second side layer comprises at least four layers of the second material forming the second side layer in an overlapping configuration.

4. The absorbent article of claim 1 wherein the first side layer has a first width, measured in the transverse direction, from the first inner edge of the first folded portion of the first side layer and a first bond area between the first side layer and the central layer is from 2 to 20 mm and wherein the second side layer has a second width, measured in the transverse direction, from the second inner edge of the second folded portion of the second side layer and a second bond area between the second side layer and the central layer is from 2 to 20 mm.

5. The absorbent article of claim 1 wherein the first folded portion of the first side layer has an unattached portion which has a first width in the transverse direction from 3 to 30 mm and wherein the second folded portion of the second side layer has an unattached portion which has a second width in the transverse direction from 3 to 30 mm.

6. The absorbent article of claim 1 wherein the first folded portion of the first side layer has a first width in the transverse direction between the first inner edge forming the first fold of the first folded portion and a first exterior fold of the first folded portion of greater than 5 mm.

7. The absorbent article of claim 6 wherein the first folded portion of the first side layer has a first width in the transverse direction between the first fold of the first folded portion and the first exterior fold of the first folded portion from 5 mm to 30 mm.

8. The absorbent article of claim 1 wherein the second folded portion of the second side layer has a second width in the transverse direction between the second inner edge forming the first fold of the second folded portion and a second exterior fold of the second folded portion of greater than 5 mm.

9. The absorbent article of claim 8 wherein the second folded portion of the second side layer has a second width in the transverse direction between the first fold of the second folded portion and the second exterior fold of the second folded portion from 5 mm to 30 mm.

10. The absorbent article of claim 1 wherein the first side layer further comprises a first embossment and wherein the second side layer further comprises a second embossment.

11. The absorbent article of claim 10 wherein the central layer further comprises a third embossment.

12. The absorbent article of claim 1 further comprising a surge layer.

\* \* \* \* \*